(12) United States Patent
Vaziri et al.

(10) Patent No.: US 10,317,390 B2
(45) Date of Patent: Jun. 11, 2019

(54) RECORDING DYNAMICS OF CELLULAR PROCESSES

(71) Applicant: University of Vienna, Vienna (AT)

(72) Inventors: Alipasha Vaziri, Vienna (AT); Robert Prevedel, Vienna (AT)

(73) Assignee: UNIVERSITY OF VIENNA, Vienna (AT)

(*) Notice: Subject to any disclaimer, the term of this patent is extended or adjusted under 35 U.S.C. 154(b) by 807 days.

(21) Appl. No.: 14/846,934

(22) Filed: Sep. 7, 2015

(65) Prior Publication Data
US 2016/0069794 A1 Mar. 10, 2016

Related U.S. Application Data

(60) Provisional application No. 62/047,425, filed on Sep. 8, 2014.

(51) Int. Cl.
| | |
|---|---|
| *G01N 33/483* | (2006.01) |
| *G01J 3/44* | (2006.01) |
| *G01N 21/63* | (2006.01) |
| *G01N 21/64* | (2006.01) |
| *G02B 21/02* | (2006.01) |

(Continued)

(52) U.S. Cl.
CPC ........ *G01N 33/4833* (2013.01); *G01J 3/4406* (2013.01); *G01N 21/636* (2013.01); *G01N 21/6458* (2013.01); *G02B 21/02* (2013.01); *G02B 21/16* (2013.01); *A61B 5/4064* (2013.01); *G01N 2021/6419* (2013.01); *G01N 2021/6421* (2013.01); *G01N 2201/0635* (2013.01); *G01N 2201/0697* (2013.01); *G01N 2201/1045* (2013.01); *G02B 2207/114* (2013.01)

(58) Field of Classification Search
CPC ............ G01N 21/6458; G01N 33/582; G01N 21/6486; G01N 2201/0697
See application file for complete search history.

(56) References Cited

FOREIGN PATENT DOCUMENTS

| | | |
|---|---|---|
| WO | 20020012222 A2 | 1/2002 |
| WO | 2009064753 A1 | 5/2009 |
| WO | 2012135823 A1 | 10/2012 |

OTHER PUBLICATIONS

Cheng L.-C. et al.: "Widefiled Multiphoton Excited Florescence Microcopy for Animal Study In Vivo", Proc. of SPIE, vol. 7765, Aug. 24, 2010 (Aug. 24, 2010), PO Box 10 Bellingham WA 98227-0010, USA, pp. 77650Y-1-77650Y-7, XP040540930, DOI: 10.1117/12.864107.

(Continued)

*Primary Examiner* — Kenneth J Malkowski
(74) *Attorney, Agent, or Firm* — Hoffman & Baron, LLP

(57) ABSTRACT

Devices and methods for recording dynamics of cellular and/or biochemical processes, including a device including one or more dispersive elements configured to receive a pulsed laser beam with a spectrum of different wavelengths and disperse the spectrum of the pulsed laser beam; and one or more first elements configured to receive the dispersed spectrum of the pulsed laser beam, and generate a multiphoton excitation area in a biological sample by re-overlapping in time and space the dispersed spectrum of the pulsed laser beam on an area in the biological sample, wherein the device is configured to record at high speed changes of cellular and biochemical processes of a population of cells of the biological sample based on generation of the multiphoton excitation area in the biological sample.

29 Claims, 12 Drawing Sheets

(51) Int. Cl.
    *G02B 21/16*     (2006.01)
    *A61B 5/00*     (2006.01)

(56) References Cited

OTHER PUBLICATIONS

Daekeun Kim et al: "Three-dimensional (3D) high-speed imaging and fabrication system based on ultrafast optical pulse manipulation", Proceedings of SPIE, vol. 7183, Feb. 13, 2009 (Feb. 13, 2009), pp. 71831B-1-71831B-8, XP055031576, ISSN: 0277-786X, DOI: 10.1117/12.810910.
Durst et al: "Simultaneous spatial and temporal focusing in nonlinear microscopy", Optics Communications, North-Holland Publishing Co. Amsterdam, NL, vol. 281, No. 7, Feb. 23, 2008 (Feb. 23, 2008), pp. 1796-1805, XP022496880, ISSN: 0030-4018, DOI: 10.1016/J.OPTCOM.2007.05.071.
Losavio B. .E et al: "Two-photon microscope for multisite microphotolysis of caged neurotransmitters in acute brain slices", Journal of Biomedical Optics, vol. 14, No. 6, Dec. 31, 2009 (Dec. 31, 2009), USA, pp. 064033-1-064033-14, XP040506066.
Nakamura Aoi et al: "2D simultaneous spatial and temporal focusing as a fast-scanning two-photon excited fluorescence microscopy", 2013 Conference on Lasers and Electro-Optics Pacific RIM (CLEOPR), IEEE, Jun. 30, 2013 (Jun. 30, 2013), pp. 1-2, XP032481792, DOI: 10.1109/CLEOPR.2013.6600623.
PCT/IB2015/001963 International Search Report and Written Opinion of the International Searching Authority dated Mar. 4, 2016.
International Preliminary Report on Patentability dated Mar. 23, 2017 from International Patent Application No. PCT/IB2015/001963.

RECORDING DYNAMICS OF CELLULAR PROCESSES

REFERENCE TO RELATED APPLICATIONS

This application claims the benefit of priority from U.S. Provisional Patent Application Ser. No. 62/047,425, filed on Sep. 8, 2014, and entitled "Recording Dynamics of Cellular Processes," which is incorporated by reference herein in its entirety.

TECHNICAL FIELD

This disclosure relates to recording the dynamics of cellular processes.

BACKGROUND

A biological sample, such as an organism, includes cells that perform various activities. Other biochemical processes also may be performed by the organism.

BRIEF DESCRIPTION OF THE DRAWINGS

Like reference symbols in different figures represent like elements.

DETAILED DESCRIPTION

Figure 1:
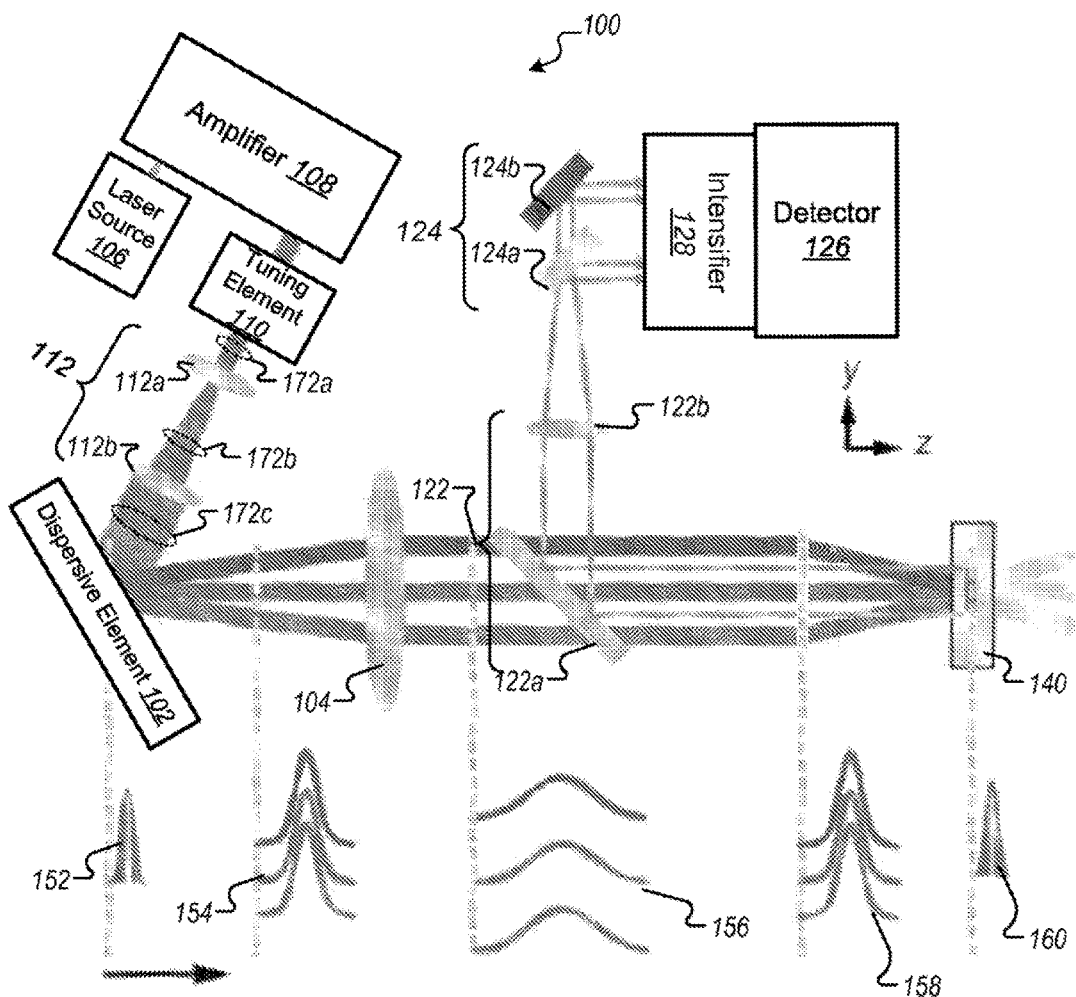
FIGS. 1 and 2 illustrate example components of a first system for recording dynamics of cellular and/or biochemical processes of a population of cells of a biological sample.

Recent research in biomedical technologies have been targeted towards obtaining information about detailed connectivity between cells to perform various activities, for example, how a network of neurons interconnect and engage in dynamic activities. It may be useful to come up with a high-resolution imaging technique that is capable of recording the dynamics (also referred to interchangeably as "changes" in the following sections) of cellular or biochemical processes in a biological sample, where the technique is capable of recording the dynamics of small or large groups of cells at the resolution of a single cell and with high-speeds.

Towards this end, this disclosure describes devices, systems and associated methods for recording the dynamics or changes of cellular or biochemical processes of a population of cells of a biological sample. The biological sample may correspond to any organism, including, for example, worms, fish, mammals, or some other suitable organism. The dynamics of cellular or biochemical processes may include, for example, activity of neurons associated with brain functions, cardiovascular activities, or some other suitable activity. Sections of the biological sample that are to be recorded may be excited using a light source, for example, a laser beam. The recording may be performed in high-speed, for example, successive images may be generated or captured simultaneously, or near-simultaneously in an order of seconds or fractions of seconds. The population of cells may include a large population of cells of the biological sample, for example, in the range of tens to thousands, or millions, of cells. In some implementations, the population of cells may encompass an entire organism, and the recording may capture the dynamics of cellular or biochemical processes of a complete mammal.

To facilitate the recording of changes of the cellular and/or biochemical processes, molecular reporters may be artificially introduced in the biological sample, for example, in the cells. The recording of the multiphoton excitation and subsequent optical readout may be based on light emission properties of the molecular reporters.

The devices, systems and methods that are described herein for recording of the dynamics or changes of cellular or biochemical processes of a population of cells of a biological sample using molecular reporters may find applicability in various situations. For example, the devices, systems and methods may be used to serve applications in neuroscience. Additionally or alternatively, the devices, systems and methods may be configured to serve discovery of new drugs, therapeutic agents or strategies. Additionally or alternatively, the devices system and methods may be configured to serve applications in stem cell research. Additionally or alternatively, the devices system and methods may be configured to serve applications in cancer research.

In a general aspect, a device comprises one or more dispersive elements that are configured to receive a pulsed laser beam with a spectrum of different wavelengths and disperse the spectrum of the pulsed laser beam. The device also includes one or more first elements that are configured to receive the dispersed spectrum of the pulsed laser beam, and generate a multiphoton excitation area in a biological sample by re-overlapping in time and space the dispersed spectrum of the pulsed laser beam on an area in the biological sample. The device is configured to record at high speed changes of cellular and biochemical processes of a population of cells of the biological sample based on generation of the multiphoton excitation area in the biological sample.

Particular implementations may include one or more of the following features. The device may include a first amplifier that is configured to amplify the pulsed laser beam, wherein the pulsed laser beam amplified by the first amplifier may be used at the dispersive element. The device may include a wavelength tuning element that is configured to tune the central wavelength of the pulsed laser beam amplified by the first amplifier to an excitation wavelength of a molecular reporter associated with the biological sample. The device may include a motorized half-wave plate and a polarizing beam splitter with a shutter that are configured to attenuate the power of the pulsed laser beam at an output of the wavelength tuning element. The first amplifier may include a regenerative amplifier.

The molecular reporter may be configured to facilitate recording of the cellular or biochemical changes of the biological sample. The molecular reporter may include one or more molecules, which also may be referred to as labeling molecules, which may be artificially introduced into the cells. The changes of cellular and biochemical processes of the sample may be recorded via multiphoton excitation and subsequent optical readout of light emission properties of the artificially-introduced molecules. The molecules may be configured to readout at least one of calcium concentrations in the cells, or changes to calcium concentrations in the cells. The molecules may include proteins that are expressed by the cells by introducing genetic information to the cells. The molecules may be configured to report on at least one of membrane voltage of the cells, or changes to the membrane voltage of the cells. The molecules may be configured to report on synaptic activity in the cells. The molecules may be configured to report on metabolic activity in the cells. The molecules may be configured to report on enzymatic activity in the cells. The molecules may be configured to bind to at least one of naturally available proteins in the cells, or other molecules in the cells. The molecules may be configured to report on a stage of the cell cycle.

The multiphoton excitation area may comprise an arbitrarily-shaped excitation disc of the dispersed spectrum of the pulsed laser beam. Spectral components of the pulsed laser beam may overlap in time and space in a focal region of the first element.

A first element may include at least one of a grating, a prism, a lens or a microscope objective lens that are configured to generate the multiphoton excitation area in the biological sample by imaging onto the biological sample an area on the dispersive element illuminated by the pulsed laser beam.

The high speed recording may include near simultaneous imaging of the cellular or biochemical changes within a single plane of the biological sample. The near-simultaneous imaging may include imaging in an order of seconds to picoseconds.

The multiphoton excitation area may include a wide-field excitation disc with one of a predetermined diameter or a predetermined axial confinement. The predetermined diameter or the predetermined axial confinement may be user-configurable. At least one of the predetermined diameter or the predetermined axial confinement may be in a range that is in an order of 1 µm to 1 mm.

In another aspect, cellular or biochemical changes of a population of cells of a biological sample are imaged at high-speed by providing a pulsed laser beam with a spectrum of different wavelengths at a dispersive element. The spectrum of the pulsed laser beam is dispersed using the dispersive element. A multiphoton excitation area based on the dispersed spectrum of the pulsed laser beam is generated using a first element. The multiphoton excitation area is applied to a biological sample using the first element. An imaging detector array is used to capture information in parallel about the cellular or biochemical changes of a population of cells of the biological sample included in the multiphoton excitation area. The information about the cellular or biochemical changes is captured at a resolution of a single cell.

Particular implementations may include one or more of the following features. The pulsed laser beam may be generated using a laser source. The pulsed laser beam may be amplified using a first amplifier. A central wavelength of the pulsed laser beam amplified by the first amplifier may be tuned using a wavelength tuning element to an excitation wavelength of a molecular reporter that produces a signal associated with the cellular or biochemical changes of the cells of the biological sample. The pulsed laser beam tuned by the wavelength tuning element may be provided at the dispersive element.

The molecular reporter may include molecules, which also may be referred to as labeling molecules, which may be artificially introduced into the cells. The changes of cellular and biochemical processes of the sample may be recorded via multiphoton excitation and subsequent optical readout of light emission properties of the artificially-introduced molecules.

The molecules may be configured to readout at least one of calcium concentrations in the cells, or changes to calcium concentrations in the cells. The molecules may include proteins that are expressed by the cells by introducing genetic information to the cells. The molecules may be configured to report on at least one of membrane voltage of the cells, or changes to the membrane voltage of the cells. The molecules may be configured to report on synaptic activity in the cells. The molecules may be configured to report on metabolic activity in the cells. The molecules may be configured to report on enzymatic activity in the cells. The molecules may be configured to bind to at least one of naturally available proteins in the cells, or other molecules in the cells. The molecules may be configured to report on a stage of the cell cycle.

The power of the pulsed laser beam tuned by the wavelength tuning element may be attenuated using an attenuating element. A cross-sectional area of the pulsed laser beam may be modified or modulated using a second optical element. The pulsed laser beam with the modulated cross-sectional area may be provided at the dispersive element.

The attenuating element may include one of a half-wave plate and a beam splitter, or a shutter. The second optical element may include a telescope.

The first element may include at least one of a relay lens or a microscope objective that are configured to generate the multiphoton excitation area in a focal region of the microscope objective.

In another aspect, a device includes one or more manipulating elements configured to manipulate spatial or angular displacement of a pulsed laser beam that includes a spectrum of different wavelengths. The device also includes one or more first elements configured to modify the shape of the pulsed laser beam. The device further includes one or more dispersive elements configured to disperse the spectrum of the pulsed laser beam. In addition, the device includes one or more second elements configured to generate a multiphoton excitation area based on the dispersed spectrum of the pulsed laser beam and apply the multiphoton excitation area to a biological sample. The device is configured to record at high-speed changes of cellular or biochemical processes of a population of cells of the biological sample based on application of the multiphoton excitation area to the biological sample.

Particular implementations may include one or more of the following features. The device may be configured to perform the high-speed recording at single-cell spatial resolution for a predetermined time period.

A first element may include a spherical lens that is configured to shape an area on the dispersive element used by the manipulating device to generate a trajectory on the dispersive element that corresponds to the multiphoton excitation area in the biological sample. Recording of the cellular or biochemical changes of cells of the biological sample may be performed in two dimensions based on sequential or parallel excitation that may be limited at a time to the area in the biological sample corresponding to the generated trajectory. The generated trajectory may include a spiral path.

The multiphoton excitation area may include an arbitrarily-shaped wide-field excitation area with a predetermined axial confinement that is user-configurable in a range in an order of 1 µm to 1 mm. The arbitrarily-shaped excitation area may include a predetermined diameter that may be user-configurable. The predetermined diameter may be in a range that is in an order of 1 µm to 1 mm. The arbitrarily-shaped excitation area may include a variable diameter.

The device may comprise a detection section for detecting the changes of the cellular or biochemical processes of the cells of the biological sample. The detection section may include one or more third elements configured to separate a signal associated with the changes of the cellular or biochemical processes from the pulsed laser beam. A third element may include a dichroic mirror.

The detection section may include an array detector that is configured to generate images of the cellular or biochemical changes of the population of cells of the biological sample.

Implementations of the above techniques include methods, systems, computer program products and computer-readable media. One such system comprises one or more devices and/or components that are configured to record at high speed the changes of cellular and/or biochemical processes of cells of a biological sample based on generation of a multiphoton excitation area in the biological sample. The system also comprises a machine-readable medium for storing instructions that are executable by a processing unit and, when executed by the processing unit, are configured to cause the devices and/or components to perform one or more of the above described operations.

One such method involves performing one or more of the above described operations using devices and components for recording the changes of cellular and/or biochemical processes of a population of cells of a biological sample.

One such computer program product is suitably embodied in a non-transitory machine-readable medium that stores instructions executable by one or more processing units. The instructions are configured to cause the one or more processing units to perform one or more of the above described operations. One such computer-readable medium stores instructions that, when executed by a processing unit, are configured to cause the processing unit to perform one or more of the above described operations.

The details of one or more disclosed implementations are set forth in the accompanying drawings and the description below. Other features, aspects, and advantages will become apparent from the description, the drawings and the claims.

Figure 2:
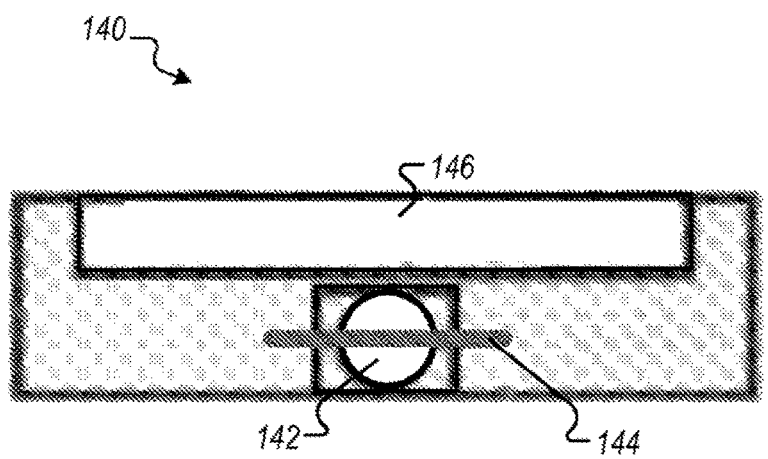

FIGS. 1 and 2 illustrate example components of a first system 100 for recording dynamics of cellular and/or biochemical processes of a population of cells of a biological sample. As shown in FIG. 1, the system 100 includes a device that is configured to record the dynamics of cellular and/or biochemical processes of the population of cells of the biological sample at high speed based on generation of a multiphoton excitation area in the biological sample. The device includes a dispersive element 102 and an optical element 104. The system 100 also includes additional components that are used for generation of the multiphoton excitation area in the biological sample, such as a laser source 106, an amplifier 108, a tuning element 110, and an optical element 112. In addition, the device of system 100 includes components that are used for recording the dynamics of the cellular and biochemical processes, such as an optical separator 122, a splitter 124, a detector 126 and an intensifier 128. Furthermore, the system 100 includes a target device 140 and a molecular reporter that is applied to the biological sample.

The dispersive element 102 is configured to disperse the spectrum of a light source. For example, the dispersive element may disperse the spectrum of a pulsed laser beam that is applied to the biological sample. The pulsed laser beam may include a spectrum of different wavelengths. The undispersed spectrum of the pulsed laser beam as received at the dispersive element is indicated by 152, while the dispersed spectrum of a pulsed laser beam following processing by the dispersive element is indicated by 154. The pulses 152, 154, 156, 158 and 160 indicate geometric dispersion of the pulsed laser beam in in temporal focusing as a function of axial position. In some implementations, there may be several dispersive elements 102 included in the device of system 100.

In some implementations, the dispersive element may spatially disperse the spectrum of the pulsed laser beam. In some implementations, the pulsed laser beam that is dispersed by the dispersive element may have a picosecond pulse or a femtosecond pulse, or some other suitable pulse duration. The dispersive element may be a grating, a prism, or some other suitable component.

The optical element 104 is configured to refocus the dispersed spectrum of the pulsed laser beam in an area of the biological sample, thereby generating a multiphoton excitation area in the biological sample. The dispersed spectrum of the pulsed laser beam processed by the optical element is indicated by 156. In some implementations, there may be several optical elements 104 included in the device of system 100.

The optical element 104 may comprise one or more discrete optical elements. In some implementations, the optical element 104 includes a lens (for example, a relay lens) and a microscope objective. In some other implementations, the optical element 104 includes a grating, a prism, or some other suitable element. The optical element 104 images an illuminated spot on the dispersive element in the biological sample. In doing so, the spectral components of the pulsed laser beam are configured to overlap in time and/or space in the focal region of the optical element 104, leading to the multiphoton excitation. Outside the focal region of the optical element, the spectral components of the pulsed laser beam do not overlap in time and/or space, thereby reducing the probability of multiphoton excitation. In some implementations, the multiphoton excitation area that is generated in the biological sample includes a two-photon excitation area. In some implementations, the excitation area includes an excitation disc. For example, a wide-field two-photon excitation area of approximately 60 µm in diameter with an axial confinement of approximately 1.9 µm may be generated in one implementation.

In some implementations, the laser source 106 is configured to generate the pulsed laser beam that is used for the generation of the multiphoton excitation area. In some implementations, the laser source 106 may include a titanium-sapphire (Ti:Sa) laser source that is configured to generate a laser beam with a pulse duration in the order of picoseconds or femtoseconds.

The amplifier 108 is configured to amplify the pulsed laser beam generated by the laser source 106. In doing so, the amplifier 108 may increase the power of the pulsed laser beam, for example, generating higher peak pulse energy that may be useful for generating the multiphoton excitation area. For example, the power of the pulsed laser beam at the output of the amplifier 108 may be in an order of milli-Joules. In some implementations, the amplifier 108 includes a regenerative amplifier. The regenerative amplifier may have a low-repetition rate.

In some implementations, the tuning element 110 is a wavelength tuning element that is configured to tune the pulsed laser beam amplified by the amplifier 108 to an excitation wavelength of a molecular reporter associated with the biological sample. In some implementations, the tuning element 110 is configured to tune the central wavelength of the pulsed laser beam. In some implementations, the tuning element 110 includes an optical parametric amplifier (OPA). In some implementations, the tuning element 110 also includes a motorized half-wave plate and a polarizing beam splitter with a shutter that are configured to attenuate the power of the pulsed laser beam at an output of the tuning element. For example, the laser power at the output of the OPA may be in an order of 20 micro-Joules ($\mu J$), which is attenuated by the motorized half-wave plate and a polarizing beam splitter to an order of 2 $\mu J$.

The molecular reporter may include artificially-introduced molecules, also referred to as labeling molecules in some implementations, which are configured to facilitate recording of the cellular or biochemical dynamics of the biological sample. The recording of the multiphoton excitation and subsequent optical readout may be based on light emission properties of the labeling molecules. In some implementations, the molecular reporter or labeling molecules may be included as part of the device that comprises the dispersive element 102 and the optical element 104.

In some implementations, the labeling molecules are configured to readout calcium concentrations in the cells, and/or changes to calcium concentrations in the cells. For example, the molecular reporter may be a nuclear-localized, genetically encoded calcium indicator such as, but not limited to, NLS-GCaMP5K, which enables recording the dynamics of individual cells of the biological sample.

In some implementations, the labeling molecules include proteins that are expressed by the cells by introducing genetic information to the cells. In some implementations, the labeling molecules are configured to bind to naturally available proteins, and/or other molecules, in the cells.

In some implementations, the labeling molecules are configured to report on membrane voltage of the cells, and/or changes to membrane voltage of the cells. In some implementations, the labeling molecules are configured to report on synaptic activity in the cells. In some implementations, the labeling molecules are configured to report on metabolic activity in the cells. In some implementations, the labeling molecules are configured to report on enzymatic activity in the cells. In some implementations, the labeling molecules are configured to report on a stage of the cell cycle.

The optical element 112 is configured to adjust the cross-sectional area of the pulsed laser beam at an output of the tuning element 110. For example, the optical element 112 may include a telescope comprising one or more lenses 112a and 112b. In some implementations, the telescope may expand the diameter of the pulsed laser beam from diameter 172a to diameter 172b, and further to diameter 172c that is applied on to the dispersive element 102. In some other implementations, the optical element 112 may contract the diameter of the pulsed laser beam, or adjust the shape of the pulsed laser beam in some other suitable form. Based on this adjustment, the multiphoton excitation area may be configured to have an arbitrary shape. In some implementations, there may be several optical elements 112 included in the system 100.

In some implementations, one or more of the laser source 106, the amplifier 108, the tuning element 110, and the optical element 112 are included as parts of the device configured to record the dynamics of cellular and/or biochemical processes of the population of cells of the biological sample, in addition to the dispersive element 102 and the optical element 104. In some implementations, these components form an imaging section of the device.

The optical separator 122 is configured to separate a signal associated with the cellular or biochemical dynamics of the biological sample from the pulsed laser beam. For example, the optical separator 122 separates a fluorescence signal corresponding to the molecular reporter from the excitation light associated with the multiphoton excitation area. The excitation light is generated by the pulsed laser beam. In some implementations, the optical separator includes a dichroic mirror and a multiphoton filter 122b.

The splitter 124 is configured to split into different channels the signal that is associated with the cellular or biochemical processes and separated by the optical separator 122. In some implementations, the splitter 124 includes a wavelength separator composed of a dichroic mirror 124a and a bandpass filter 124b that splits the fluorescence signal into two channels.

The detector 126 is configured to generate images of the cellular or biochemical dynamics of the biological sample. In some implementations, the detector includes an image capture device, such as a scientific complementary metal-oxide semiconductor (sCMOS) camera or an electron multiplying charge coupled device (EMCCD) camera, or some other suitable parallel image capture device. In some implementations, the images generated by the detector 126 are captured and/or processed using custom-written programming scripts, for example, scripts written using a suitable programming language such as LabVIEW™, or Andor Solis Basic™, or some other suitable script. The images captured and/or processed using these scripts may be stored in computer memory for subsequent processing, for example, using a processing device such as a computer.

The intensifier 128 is configured to record the cellular or biochemical signal associated with the multiphoton excitation area and relay the output of the intensifier onto the detector 126. In some implementations, the intensifier 128 includes a high-gain image intensifier that records the fluorescence signal in a wide-field manner. The intensifier 128 further includes a relay lens to image the recorded fluorescence signal on to the detector. This enables the intensifier to maintain a high signal-to-noise ratio even at short exposure times (for example, exposure times on the order of 10 milliseconds).

In some implementations, one of more of the optical separator 122, the splitter 124, the detector 126 and the intensifier 128 are included as parts of a detection section of the device configured to record the dynamics of cellular and/or biochemical processes of the population of cells of the biological sample, in addition to the components of the imaging section of the device. In some implementations, the device and other components of the system 100 may be interfaced with existing microscopes and/or light sources for recording the dynamics of cellular or biochemical processes.

The target device 140 includes the biological sample. In some implementations, the dimensions of the target device may be different from that shown in FIG. 1. For example, the target device may be large enough to accommodate an entire organism, such as a mammal. FIG. 2 shows details of an example target device 140. As shown, the target device may be a microfluidic chip. The target device 140 includes a holding section 142 where the biological sample is placed. The multiphoton excitation area applied to the target device is indicated by 144.

In some implementations, a fluid (for example, but not limited to, oxygen) is supplied to the target device to excite the biological sample. The fluid may be supplied in the chamber 146.

In some implementations, the device and other components of system 100 may be used to serve applications in neuroscience, for example, but not limited to, mapping chemosensory neuronal circuits in a nervous system. The system 100 may combine controlled sensory stimulation with unbiased fast volumetric neuronal recording capable of capturing, at single-cell resolution, the activity of the majority of the neurons in the brain of an entire organism. Additionally or alternatively, the device and components of system 100 may be configured to serve discovery of one or more drugs, therapeutic agents, or therapeutic strategies. Additionally or alternatively, the device and components of system 100 may be configured to serve applications in stem cell research. Additionally or alternatively, the device and components of system 100 may be configured to serve applications in cancer research.

Figure 3:
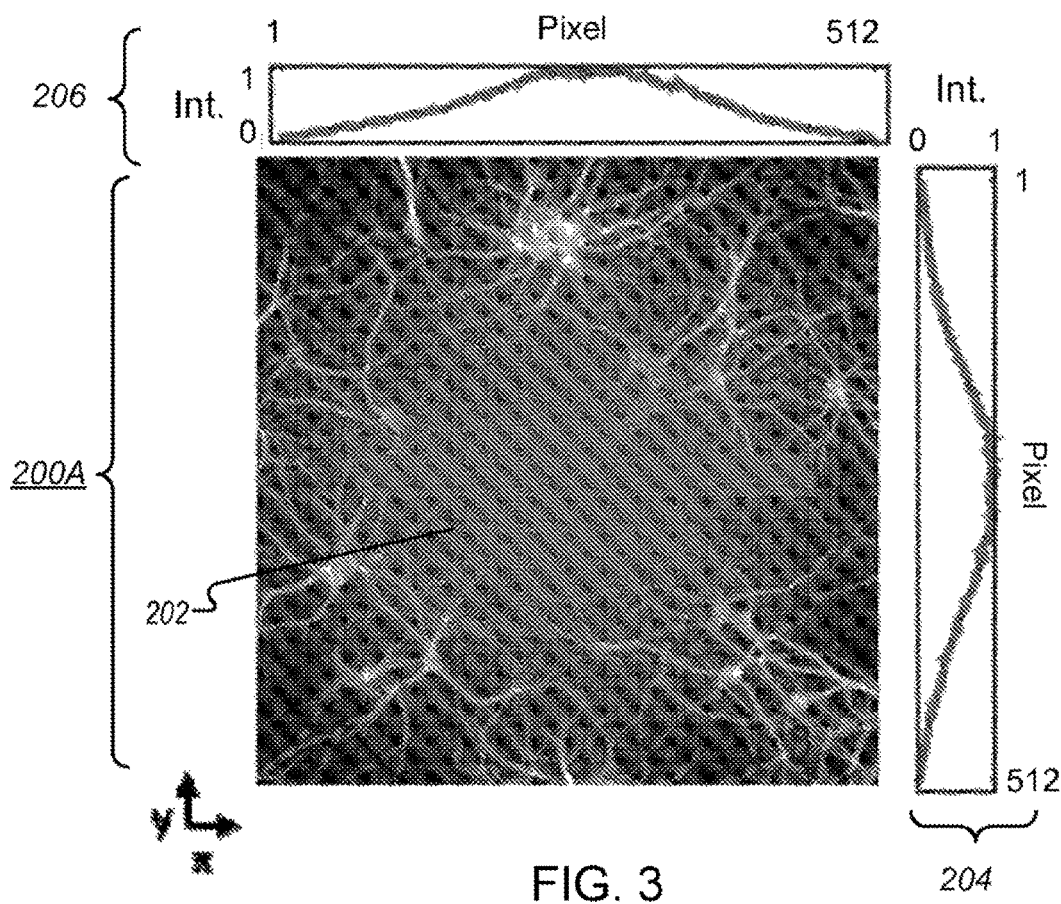
FIGS. 3-5 illustrate characteristics of an example multiphoton excitation area applied to a biological sample.
Figure 4:
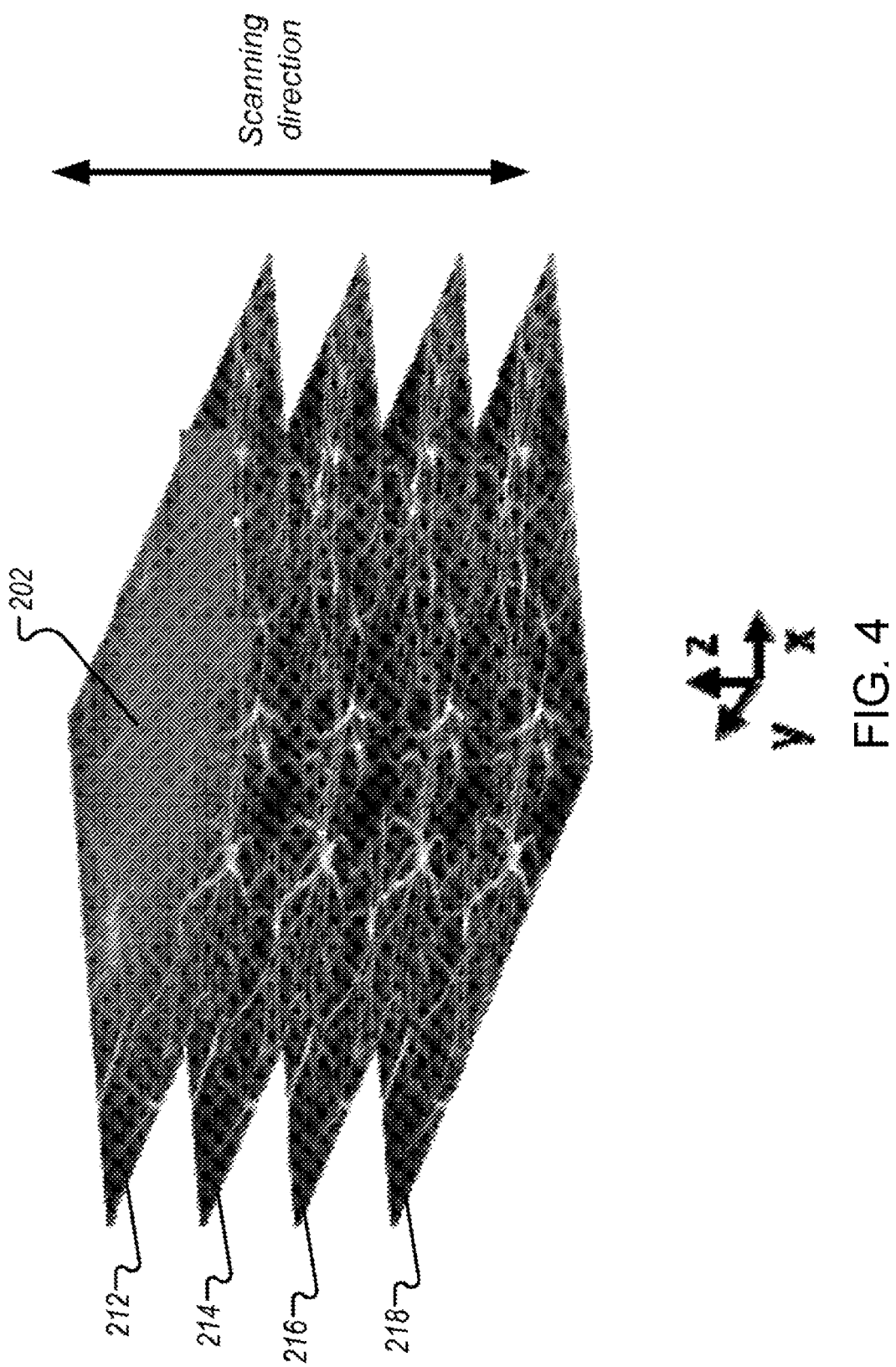
Figure 5:
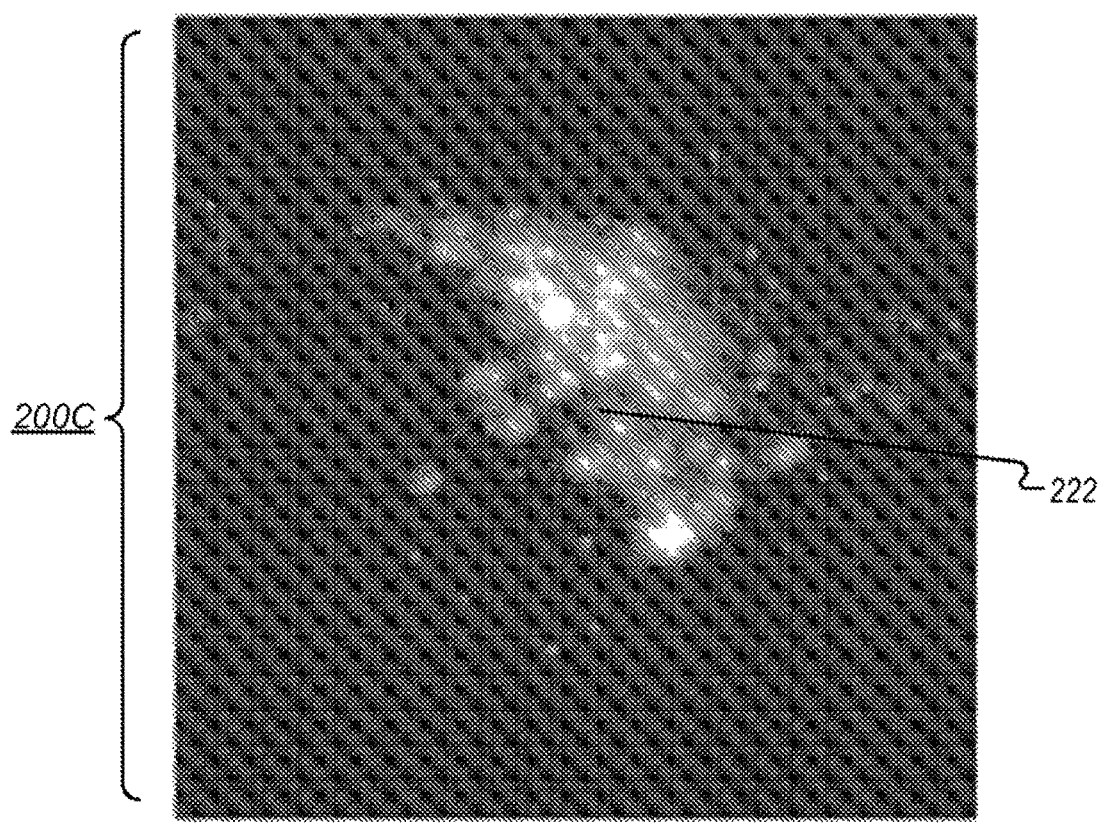

FIGS. 3-5 illustrate characteristics of an example multiphoton excitation area applied to a biological sample. The multiphoton excitation area shown in these figures may be generated using the system 100. FIG. 3 shows a two-dimensional cross-section 200A of a portion of the biological sample that is treated using the system 100. In the illustrated example, the cross-section encompasses 512×512 square pixels. The multiphoton excitation area 202 is formed in the biological sample encompassing a population of cells (such as, but not limited to, neurons). The Gaussian intensity pixel distribution of the fluorescence signal associated with the multiphoton excitation area 202 in the x-axis is indicated by 206, and in the y-axis is indicated by 204.

FIG. 5 illustrates the intensity of the fluorescence signal 222 associated with the molecular reporter that is generated due to the dynamics of the cellular and/or biochemical processes of the biological sample. The fluorescence signal 222 may be recorded using the system 100. The cross-sectional area 200C may be similar to the cross-section 200A of the portion of the biological sample that is treated using the system 100. The multiphoton excitation area 202 may be applied to the biological sample to record the fluorescence signal 222.

The system 100 may be applied to perform three-dimensional imaging of neuronal activity in a large portion of the brain of an organism. An example of such a system and results obtained by the example system are illustrated in FIGS. X1, X2, X3, X4 and X5 of U.S. Provisional Patent Application Ser. No. 62/047,425, along with their associated description, which was incorporated by reference above. In U.S. Provisional Patent Application Ser. No. 62/047,425, FIGS. X1(a)-X1(f) illustrate volumetric fluorescence imaging using wide-field two-photon light sculpting, FIGS. X2(a)-X2(r) illustrate in vivo characterization of NLS-GCaMP5K, FIGS. X3(a)-X3(d) illustrate brain-wide wide-field temporal focusing (WF-TeFo) $Ca^{2+}$ imaging in *C. elegans*, FIGS. X4(a)-X4(e) illustrate time-series correlations between neurons, and FIGS. X5(a)-X5(f) illustrate WF-TeFo $Ca^{2+}$ imaging in worms during chemosensory stimulation. The system 100 may be similarly applied to perform high-speed (such as simultaneous and/or near-simultaneous) two- or three-dimensional imaging of cellular or biochemical activity of any other organism. The images may be generated and/or recorded for a population of cells ranging from tens to millions, with the imaging performed at a resolution of a single-cell.

Figure 6:
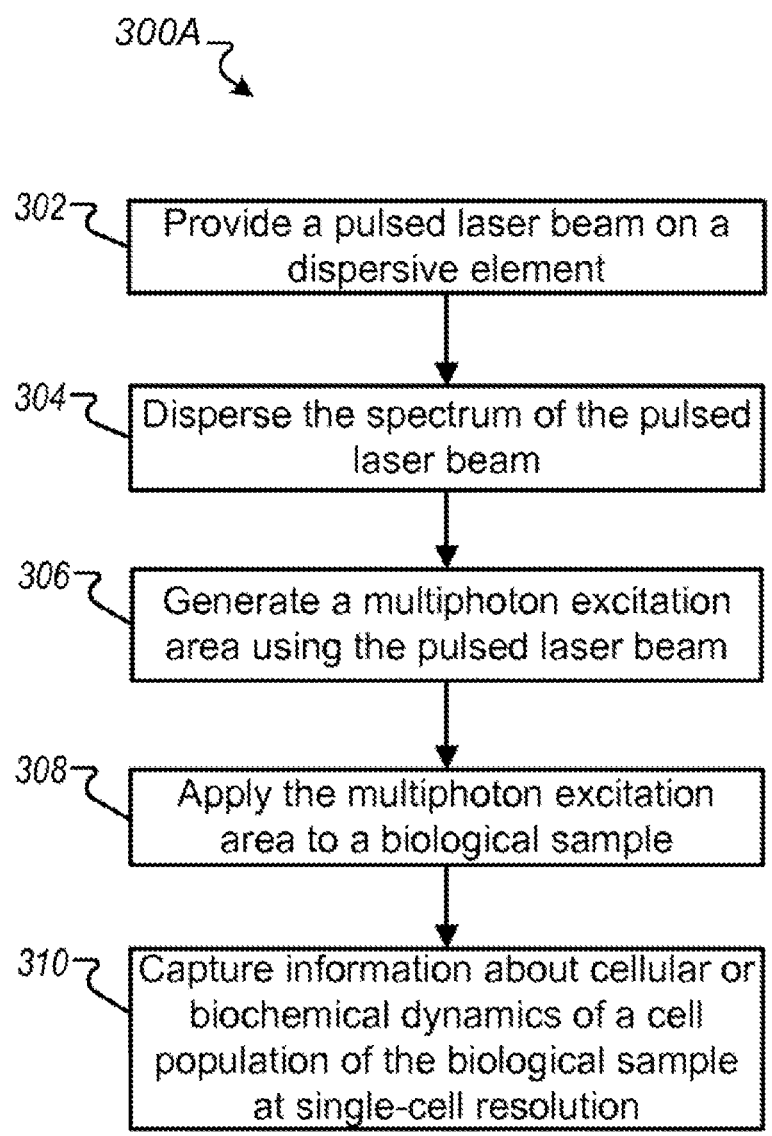
FIGS. 6-8 are flow charts illustrating example processes for recording at high speed the dynamics of cellular and/or biochemical processes of a population of cells of a biological sample.
Figure 7:
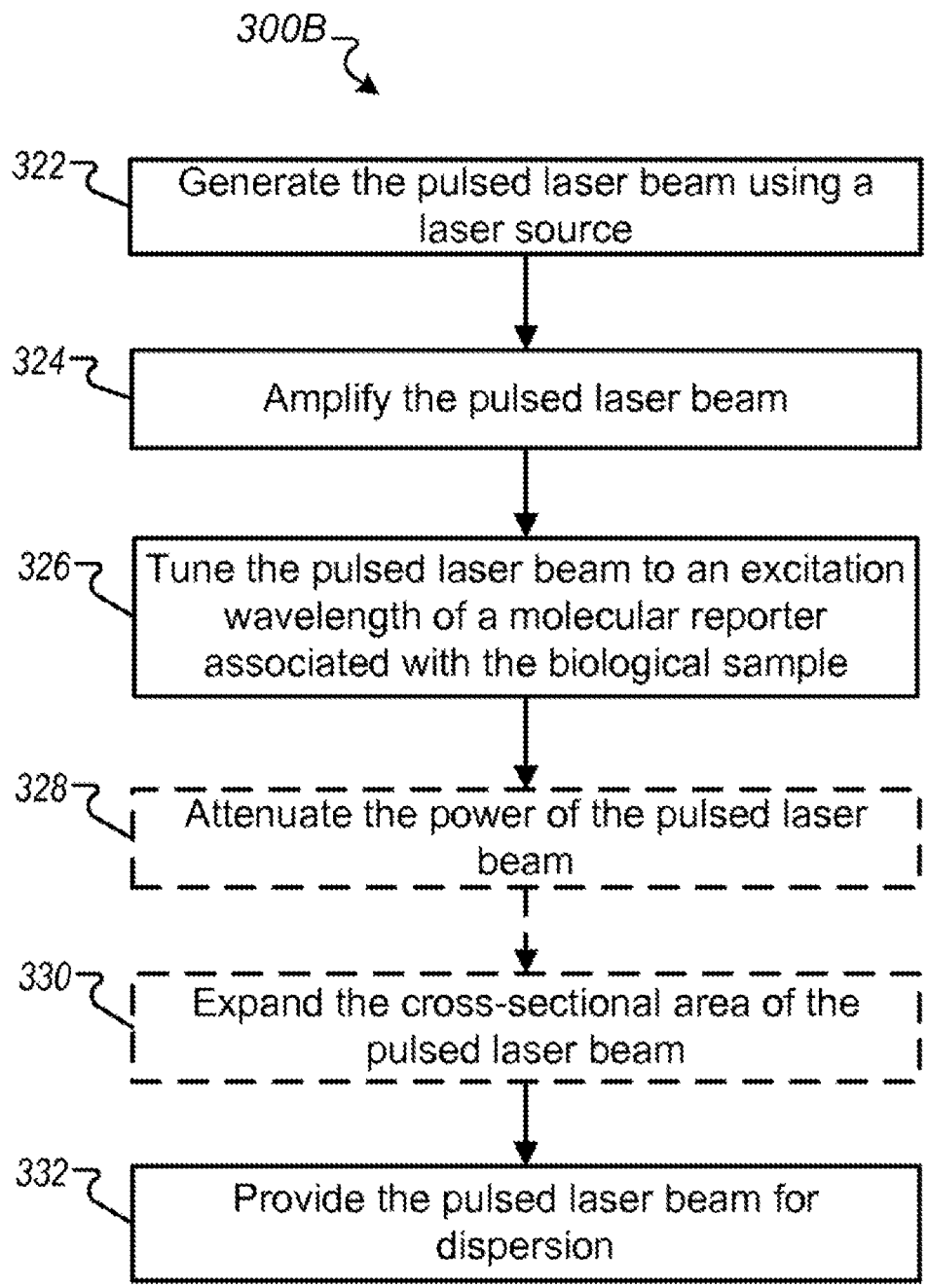
Figure 8:
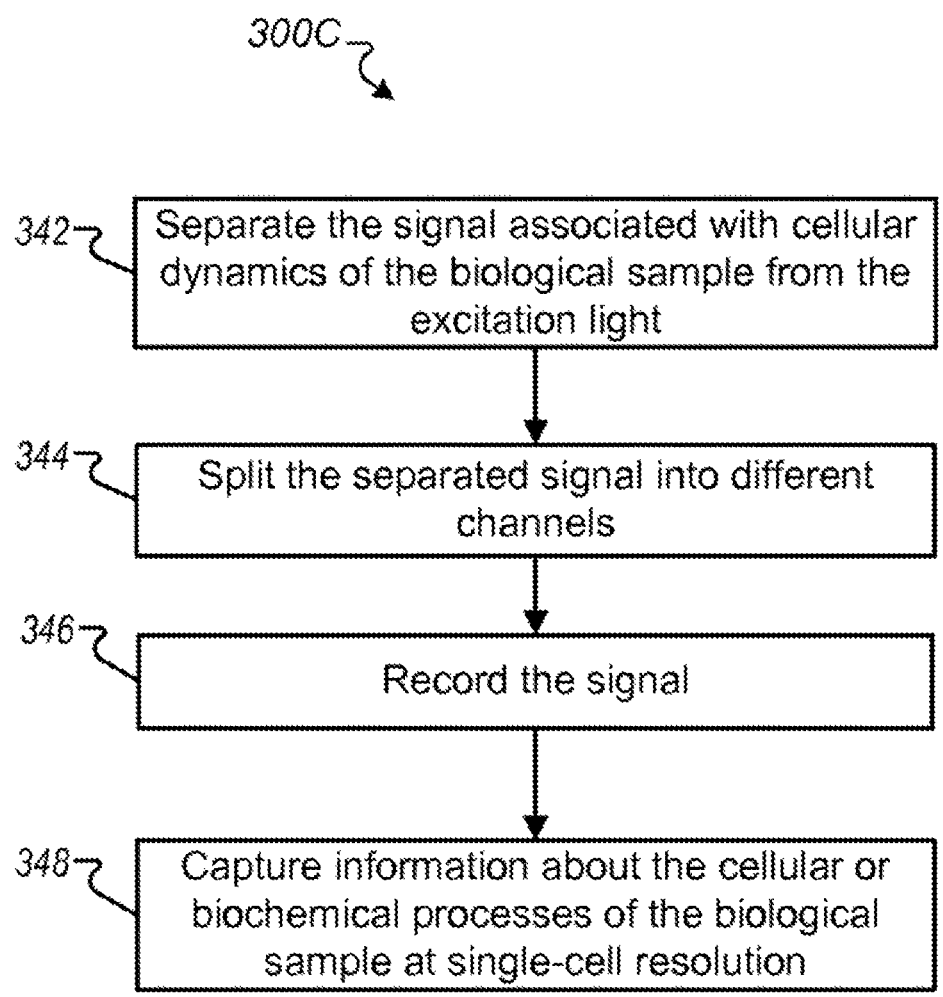

FIGS. 6-8 are flow charts illustrating example processes 300A, 300B and 300C for recording at high speed the dynamics of cellular and/or biochemical processes of a population of cells of a biological sample. The processes 300A, 300B or 300C, or some suitable combination of these, may be used to image the cellular or biochemical activity of an organism using the system 100. Accordingly, the following section describes the processes 300A, 300B and 300C as being performed by components of the system 100. However, the processes also may be performed by other systems or system configurations.

In some implementations, one or more of the processes 300A, 300B and/or 300C are implemented using a processing device, for example, a computer, a server, a mechanized device such as a robot, or some other suitable device. The processing device may include one or more processing units that execute instructions for operating the various components of the system 100 to generate the multiphoton excitation area in the biological sample, and record images of the dynamics of cellular and/or biochemical processes of cells of the biological sample. The processing unit may be a microprocessor or microcontroller, a field-programmable gate array (FPGA), a digital signal processor (DSP), or some other suitable unit that is capable of processing instructions and/or data.

In some implementations, the instructions and recorded data (such as the captured images) may be stored in memory associated with the processing device. The memory may be one of a hard disk, flash memory, read-only memory (ROM), random access memory (RAM), or some suitable combination of these, or some other memory that is capable of storing instructions and/or data.

In some implementations, the instructions may be configured by a user, such as, but not limited to, an operator of the system 100 using a user input interface (for example, a keyboard and/or a mouse coupled to the processing device). The instructions may be configured and/or generated using some suitable form, for example, a programming language or script such as LabVIEW™, Andor Solis Basic™, MetaMorph™, Molecular Devices™, Universal Imaging™, or some other suitable method.

The process 300A illustrated in FIG. 6 describes recording at high speed the dynamics of cellular and/or biochemical processes of a population of cells of a biological sample. At 302, a pulsed laser beam is provided on a dispersive element. For example, a pulsed laser beam may be provided at an area of the dispersive element 102. The pulsed laser beam may be generated by the laser source 106, amplified by the amplifier 108, and tuned by the tuning element 110. The shape of the pulsed laser beam also may be adjusted by the optical element 112 before being provided on the dispersive element 102.

The spectrum of the pulsed laser beam is dispersed at 304. For example, the dispersive element 102 may spatially disperse the spectrum of the pulsed laser beam. By dispersing the spectrum of the pulsed laser beam, the dispersive element 102 may split the pulsed laser beam into its individual component wavelengths.

At 306, a multiphoton excitation area is generated using the pulsed laser beam. For example, the optical element 104 refocuses the pulsed laser beam dispersed by the dispersive element 102 into the focal region of the optical element 104, generating the multiphoton excitation area.

At 308, the multiphoton excitation area is applied to a biological sample. For example, the optical element 104 images the multiphoton excitation area in a biological sample that is placed in the target device 140. The multiphoton excitation area imaged in the biological sample may be similar to the multiphoton excitation area 202.

Information about the cellular or biochemical dynamics of a cell population of the biological sample is captured at single-cell resolution at 310. For example, one or more of the components 122, 124, 126, or 128 may be used to record information about cellular or other biochemical activity of a population of cells of the biological sample in the target device 140. The information, such as images, may be recorded for the multiphoton excitation area that is imaged in the biological sample using one or more of the components 102, 104, 106, 108, 110, or 112.

The process 300B illustrated in FIG. 7 describes the generation and processing of the pulsed laser beam before dispersion by the dispersive element. In some implementations, the process 300B may be used in conjunction with the process 300A, while in other implementations they may be used separately.

At 322, the pulsed laser beam is generated using a laser source. For example, the laser source 106 may be operated to generate a laser beam with a pulse duration in the range of picoseconds or femtoseconds.

The pulsed laser beam is amplified at 324. For example, the amplifier 108 may be used to receive the pulsed laser beam generated by the laser source 106 and increase the power of the pulsed laser beam.

The pulsed laser beam may be tuned to an excitation wavelength of a molecular reporter associated with the biological sample at 326. For example, the tuning element 110 may tune the pulsed laser beam amplified by the amplifier 108 to an excitation wavelength of the molecular reporter (for example, but not limited to, NLS-GCaMP5K) that is used to note the changes associated with the cells or biochemical processes of the biological sample.

In some implementations, the power of the pulsed laser beam is attenuated at 328. For example, a motorized half-wave plate and a polarizing beam splitter with a shutter that are coupled to the tuning element 110 may be used to attenuate the power of the pulsed laser beam at an output of the tuning element to a range in the order of units of micro-Joules.

In some implementations, the cross-sectional area of the pulsed laser beam is expanded at 330. For example, the optical element 112 may be used to adjust the cross-sectional area of the pulsed laser beam at an output of the tuning element 110. The optical element 112 may expand the diameter of the pulsed laser beam from diameter in some implementations, while in other implementations, the optical element may contract the diameter of the pulsed laser beam, or adjust the shape of the pulsed laser beam in some other arbitrary form.

The pulsed laser beam is provided for dispersion at 332. For example, the optical element 112 may illuminate an area of the dispersive element 102 using the pulsed laser beam with the adjusted cross-sectional area.

The process 300C illustrated in FIG. 8 describes the detection and recording of information about the dynamics of cellular or biochemical processes of the biological sample based on the multiphoton excitation area formed in the biological sample. In some implementations, the process 300C may be used in conjunction with the process 300A or the process 300B, or both, while in other implementations the different processes may be used separately.

At 342, the signal associated with cellular dynamics of the biological sample is separated from the excitation light. For example, the optical separator 122 may separate a fluorescence signal corresponding to the molecular reporter used with the biological sample from the excitation light generated by the pulsed laser beam. As described previously, the molecular reporter may include one or more molecules, such as labeling molecules, which are artificially introduced into the cells. The changes of cellular and biochemical processes of the sample may be recorded via multiphoton excitation and subsequent optical readout of light emission properties of the artificially-introduced molecules.

The molecules may be configured to readout at least one of calcium concentrations in the cells, or changes to calcium concentrations in the cells. The molecules may include proteins that are expressed by the cells by introducing genetic information to the cells. The molecules may be configured to report on at least one of membrane voltage of the cells, or changes to the membrane voltage of the cells. The molecules may be configured to report on synaptic activity in the cells. The molecules may be configured to report on metabolic activity in the cells. The molecules may be configured to report on enzymatic activity in the cells. The molecules may be configured to bind to at least one of naturally available proteins in the cells, or other molecules in the cells. The molecules may be configured to report on a stage of the cell cycle.

The separated signal is split into different channels at 344. For example, the splitter 124 may split the fluorescence signal separated by the optical separator 122 into different channels.

The signal is recorded at 346. For example, the intensifier 128 may record, corresponding to the multiphoton excitation area, the fluorescence signal associated with the molecular reporter.

At 348, information about the cellular or biochemical processes of the biological sample is captured at single-cell resolution. For example, the intensifier may relay the recorded fluorescence signal onto the detector 126. The detector 126 may generate images of the dynamics of cellular or biochemical processes of the biological sample using an image sensor. The images may be generated with a resolution in the order of a single cell. These images may be captured using scripts and processed, or stored for post-processing.

Figure 9:
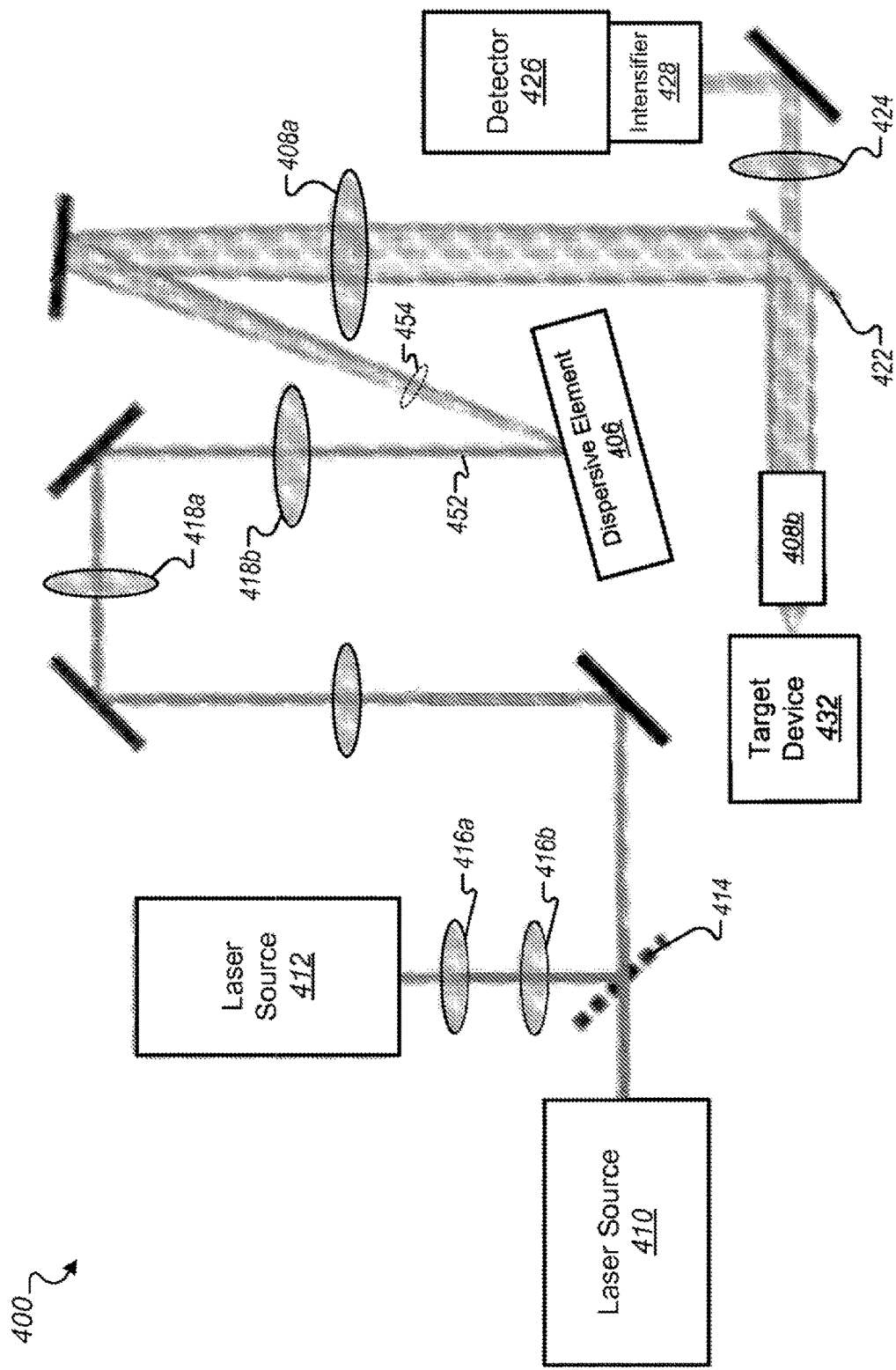
FIG. 9 illustrates example components of a second system for recording dynamics of cellular and/or biochemical processes of a population of cells of a biological sample.

FIG. 9 illustrates example components of a second system 400 for recording changes of cellular and/or biochemical processes of a population of cells of a biological sample. The system 400 includes a device that is configured to record the dynamics of cellular and/or biochemical processes of the population of cells of the biological sample at high speed (such as simultaneous or near-simultaneous in the order of nanoseconds or picoseconds) based on generation of a multiphoton excitation area in the biological sample. The device includes a dispersive element 406 and a first element 408. The first element 408 includes one or more components, such as lens 408a and/or microscope objective 408b.

The system 400 also includes additional components that are used for generation of the multiphoton excitation area in the biological sample, such as laser sources 410 and/or 412. In addition, the device of system 400 includes components that are used for recording the dynamics of the cellular and biochemical processes, such as a second element 422, a third element 424, a detector 426 and an intensifier 428. Furthermore, the system 100 includes a target device 432. In some implementations, the system includes a molecular reporter that is used for facilitating the recording of the changes of cellular and/or biochemical processes of the biological sample.

The dispersive element 406 is configured to disperse the spectrum of a light source. For example, the dispersive element may disperse the spectrum of the pulsed laser beam that is applied to the biological sample. The undispersed spectrum of the pulsed laser beam as received at the dispersive element is indicated by 452, while the dispersed spectrum of a pulsed laser beam following processing by the dispersive element is indicated by 454.

In some implementations, the dispersive element 406 may spatially disperse the spectrum of the pulsed laser beam. In some implementations, the pulsed laser beam that is dispersed by the dispersive element may have a picosecond pulse or a femtosecond pulse, or some other suitable pulse duration. The dispersive element 406 may be a grating, a prism, or some other suitable component. In some implementations, there may be several dispersive elements 406 included in the device of system 400.

The first element 408 is configured to refocus the dispersed spectrum of the pulsed laser beam in an area of the biological sample, thereby generating a multiphoton excitation area in the biological sample. In some implementations, the first element 408 includes a lens 408a (for example, a relay lens) and a microscope objective 408b. The lens 408a in conjunction with the microscope objective 408b images an illuminated spot on the dispersive element 406 in the biological sample. In doing so, the spectral components of the pulsed laser beam are configured to overlap in time and/or space in the focal region of the optical element 104, leading to the multiphoton excitation. Outside the focal region of the optical element, the spectral components of the pulsed laser beam do not overlap in time and/or space, thereby reducing the probability of multiphoton excitation. In some implementations, there may be several first elements 408 included in the device of system 400.

In some implementations, the multiphoton excitation area includes an arbitrarily-shaped excitation area with a predetermined axial confinement. In some implementations, the arbitrarily-shaped excitation area may include a predetermined diameter, while in other implementations, the arbitrarily-shaped excitation area may include a variable diameter.

In some implementations, the system 400 includes one or more laser sources 410 and/or 412, which are configured to generate the pulsed laser beam for the multiphoton excitation area. In some implementations, the laser source 410 and/or the laser source 412 may include a titanium-sapphire (Ti:Sa) laser source that is configured to generate a laser beam with a pulse duration in the order of picoseconds or femto seconds. In some implementations, the laser source 410 and/or the laser source 412 may include a regenerative amplifier in combination with an optical system that is configured to tune the wavelength of the pulsed laser beam. In some implementations, the system 400 may switch between the laser source 410 and the laser source 412 using a flip mirror 414.

In some implementations, one or more of the laser source 410 and/or the laser source 412 are included as parts of the device configured to record the dynamics of cellular and/or biochemical processes of the population of cells of the biological sample, in addition to the dispersive element 406 and the first element 408. In some implementations, these components form an imaging section of the device.

The second element 422 is configured to separate a signal associated with the cellular or biochemical dynamics of the biological sample from the pulsed laser beam. For example, the optical separator 422 separates a fluorescence signal corresponding to the molecular reporter associated with the cellular dynamics from the excitation light associated with the multiphoton excitation area. The excitation light is generated by the pulsed laser beam. In some implementations, the optical separator includes a dichroic mirror.

The third element 424 is configured to propagate the signal separated by the second element 422 onto a detection plane of a detector 426. In some implementations, the fourth element 426 includes a tube lens.

The detector 426 is configured to generate images of the cellular or biochemical dynamics of the biological sample. In some implementations, the detector 426 includes an image capture device, such as a scientific complementary metal-oxide semiconductor (sCMOS) camera or an electron multiplying charge coupled device (EMCCD) camera, or some other suitable image capture device. In some implementations, the images generated by the detector 426 are captured and/or processed using custom-written programming scripts, for example, scripts written using a suitable programming language such as LabVIEW™, or Andor Solis Basic™, or some other suitable script. The images captured and/or processed using these scripts may be stored in computer memory for subsequent processing, for example, but not limited to, using a processing device such as a computer.

The intensifier 428 is configured to record the cellular or biochemical signal associated with the multiphoton excitation area and relay the output of the intensifier onto the detector 426. In some implementations, the intensifier 428 includes a high-gain image intensifier for recording the fluorescence signal.

In some implementations, the cellular or biochemical signal associated with the multiphoton excitation area is generated by a molecular reporter that is artificially introduced into the cells. The molecular reporter may include molecules, such as labeling molecules, which may be configured to facilitate recording of the cellular or biochemical changes of the biological sample. The recording of the multiphoton excitation and subsequent optical readout may be based on light emission properties (such as the fluorescence signal) of the artificially-introduced molecules. In some implementations, the artificially-introduced molecules may be included as part of the device that includes the dispersive element 406 and the first element 408.

In some implementations, the artificially-introduced molecules are configured to readout calcium concentrations in the cells, and/or changes to calcium concentrations in the cells. For example, the molecular reporter may be a nuclear-localized, genetically encoded calcium indicator such as, but not limited to, NLS-GCaMP5K, which enables recording the dynamics of individual cells of the biological sample.

In some implementations, the molecules include proteins that are expressed by the cells by introducing genetic information to the cells. In some implementations, the molecules are configured to bind to naturally available proteins, and/or other molecules, in the cells.

In some implementations, the molecules are configured to report on membrane voltage of the cells, and/or changes to membrane voltage of the cells. In some implementations, the molecules are configured to report on synaptic activity in the cells. In some implementations, the molecules are configured to report on metabolic activity in the cells. In some implementations, the molecules are configured to report on enzymatic activity in the cells. In some implementations, the molecules are configured to report on a stage of the cell cycle.

In some implementations, the detector 426 includes an imaging sensor where the images of the cellular or biochemical process activity are generated. The imaging sensor may be a multi-pixel sensor array.

In some implementations, the detector 426 also includes a sequential readout element, such as a rolling shutter, that is configured to expose a slit portion of the imaging sensor at a time, wherein the slit portion includes a predetermined number of pixel rows and is configured to move over the imaging sensor. This may be the case, for example, when the first element used is a cylindrical lens that forms a line of multiphoton excitation in the biological sample.

In some implementations, one of more of the second element 422, the third element 424, the detector 426 and the intensifier 428 are included as parts of a detection section of the device that is configured to record the dynamics of cellular and/or biochemical processes of the population of cells of the biological sample, in addition to the components of the imaging section of the device described above. In some implementations, the device and other components of the system 400 may be interfaced with existing microscopes and/or light sources for recording the dynamics of cellular or biochemical processes.

The target device 432 includes the biological sample. In some implementations, the target device 432 may be large enough to accommodate an entire organism, such as a mammal.

As described above, the device comprising the dispersive element 406 and the first element 408, along with other components of the system 400, may be used to record the dynamics of cellular or biochemical processes of the biological sample at a high speed (such as simultaneously or near-simultaneously in the order of nanoseconds or picoseconds). The device may be configured to perform the high-speed recording at single-cell spatial resolution for a predetermined time period. The population of cells that are recorded may be in an order of tens to thousands, or millions, of cells.

In some implementations, the device and components of system 400 described above may be used to serve applications in neuroscience, for example, but not limited to, mapping chemosensory neuronal circuits in a nervous system. The system 400 may combine controlled sensory stimulation with unbiased fast volumetric neuronal recording capable of capturing, at single-cell resolution, the activity of the majority of the neurons in the brain of an entire organism. Additionally or alternatively, the device and components of system 400 may be configured to serve discovery of one or more drugs, therapeutic agents or strategies. Additionally or alternatively, the device and components of system 400 may be configured to serve applications in stem cell research. Additionally or alternatively, the device and components of system 400 may be configured to serve applications in cancer research.

Figure 10:
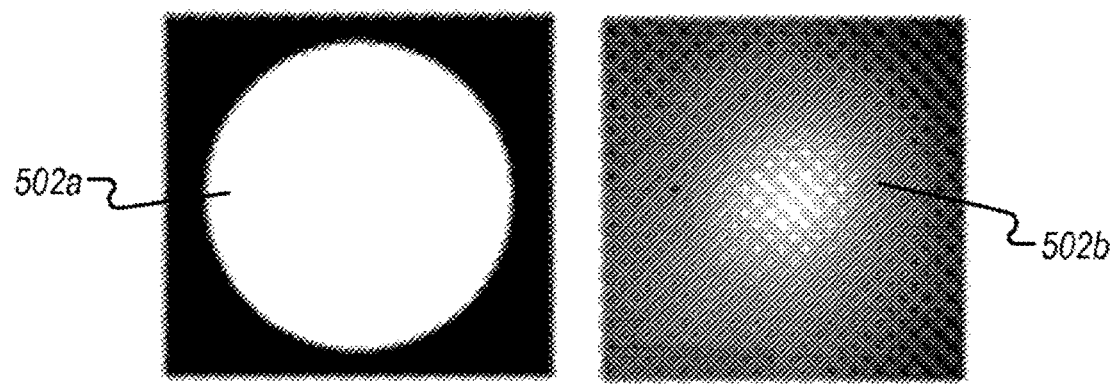
FIG. 10 illustrates example schematics of the multiphoton excitation area that may be formed in the biological sample.

FIG. 10 illustrates example schematics of the multiphoton excitation area that may be formed in the biological sample. The multiphoton excitation area shown by the schematics may be formed by the system 400. As shown, the schematic 502a corresponds to a wide-field multiphoton excitation area. 502b illustrates the wide-field excitation pattern formed in the biological sample in this configuration.

An example of the use of the system 400 for imaging a multiphoton excitation area in a biological sample and recording the dynamics of the cellular and/or biochemical processes of the biological sample, is illustrated in FIGS. 7, 8, 9, 10 and 11 of U.S. Provisional Patent Application Ser. No. 62/047,425, along with their associated description, which was incorporated by reference above. In U.S. Provisional Patent Application Ser. No. 62/047,425, FIGS. 7A-7D illustrate an experimental setup and various modalities of light sculpting microscopy, FIGS. 8A-8D illustrate trading off area versus imaging speed and fluorescence for different excitation modalities, FIGS. 9A-9C illustrate $Ca^{2+}$-imaging f acute mouse brain slices at various imaging depths and using different TeFo excitation modalities, FIGS. 10A-10G illustrate theoretical estimation of the rolling shutter effect on image quality in scattering media, and FIGS. 11A-11I illustrate experimental demonstration of improved rejection of scattering by using rolling shutter $Ca^{2+}$-imaging. As illustrated in these figures and the accompanying description, the system 400 may be applied to perform high-speed (such as simultaneous and/or near-simultaneous) two- or three-dimensional imaging of cellular or biochemical activity of an organism, where the multiphoton excitation area imaged in the organism may be of an arbitrary shape. The images may be generated and/or recorded for a population of cells ranging from tens to millions, with the imaging performed at a resolution of a single-cell.

Figure 11:
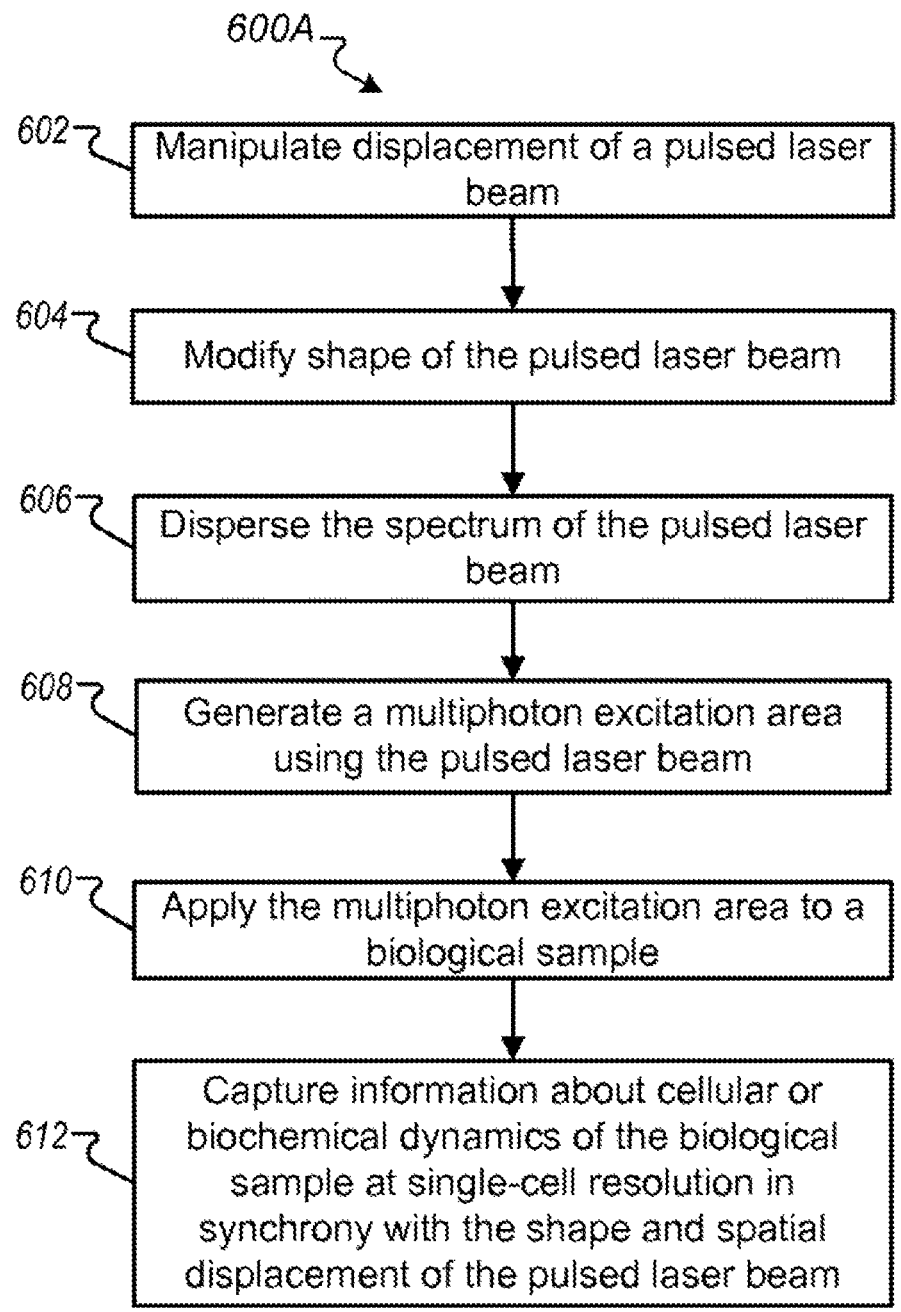
FIGS. 11-13 are flow charts illustrating example processes for recording at high speed the dynamics of cellular and/or biochemical processes of a population of cells of a biological sample.
Figure 12:
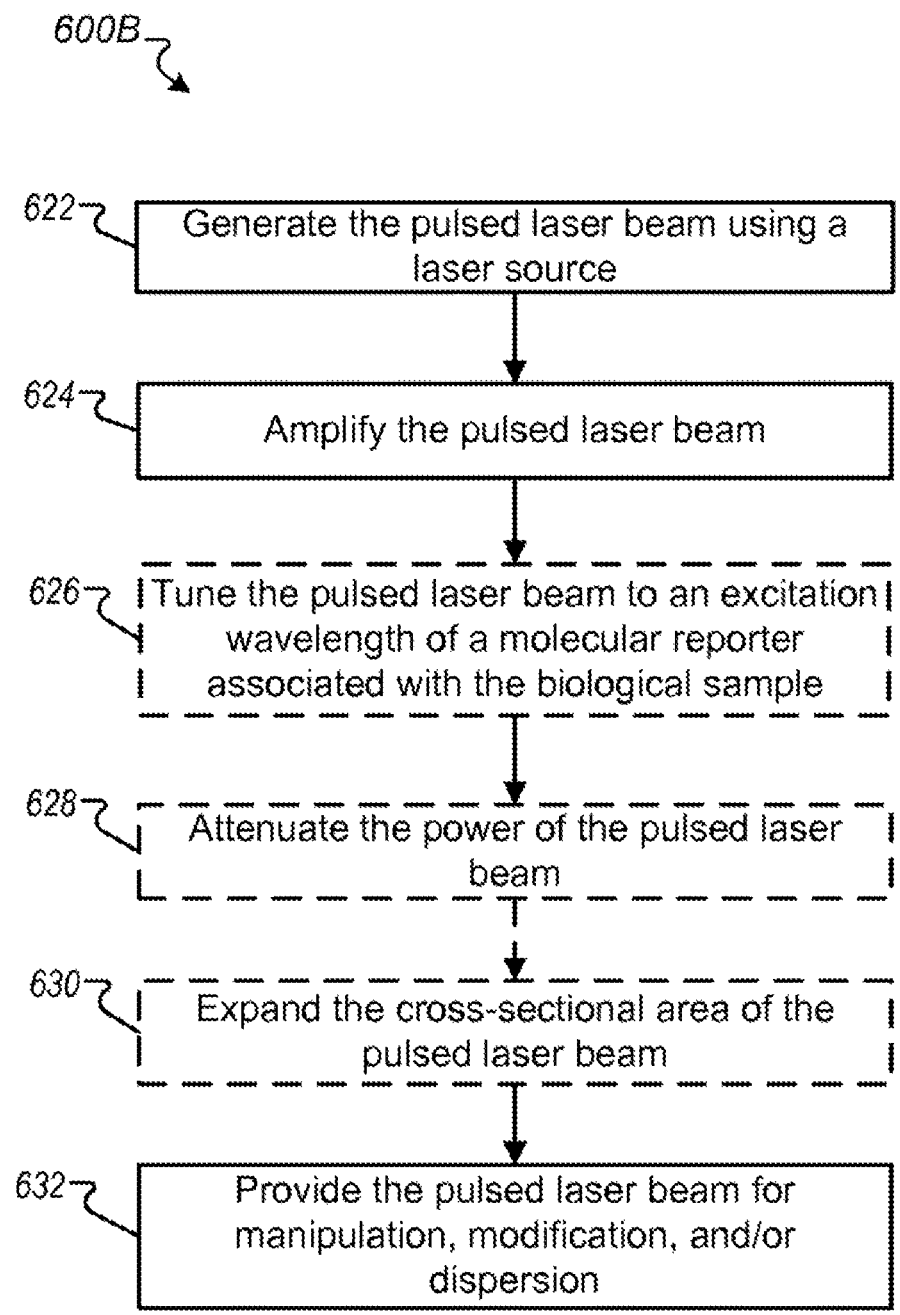
Figure 13:
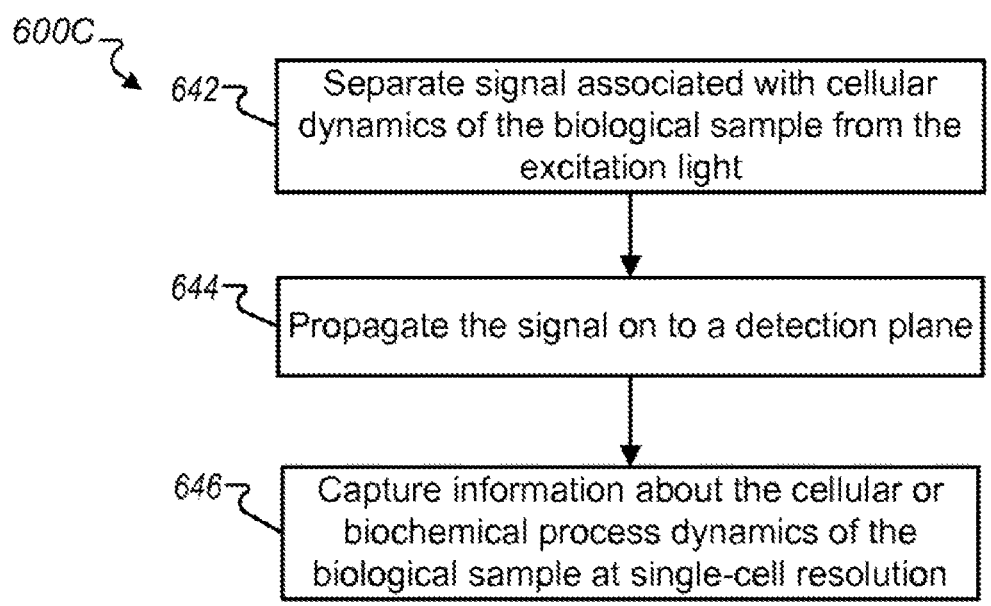

FIGS. 11-13 are flow charts illustrating example processes 600A, 600B, and 600C for recording at high speed the dynamics of cellular and/or biochemical processes of a population of cells of a biological sample. The processes 600A, 600B, or 600C, or some suitable combination of these, may be used to image the cellular or biochemical activity of an arbitrarily-shaped excitation area of an organism using the system 400. Accordingly, the following section describes the processes 600A, 600B, or 600C as being performed by components of the system 400. However, the processes also may be performed by other systems or system configurations.

In some implementations, one or more of the processes 600A, 600B, and/or 600C are implemented using a processing device, for example, but not limited to, a computer, a server, a mechanized device such as a robot, or some other suitable device. The processing device may include one or more processing units that execute instructions for operating the various components of the system 400 to generate the multiphoton excitation area in the biological sample, and record images of the dynamics of cellular and/or biochemical processes of cells of the biological sample. The processing unit may be a microprocessor or microcontroller, a field-programmable gate array (FPGA), a digital signal processor (DSP), or some other suitable unit that is capable of processing instructions and/or data.

In some implementations, the instructions and recorded data (such as the captured images) may be stored in memory associated with the processing device. The memory may be one of a hard disk, flash memory, read-only memory (ROM), random access memory (RAM), or some suitable combination of these, or some other memory that is capable of storing instructions and/or data.

In some implementations, the instructions may be configured by a user, for example, but not limited to, an operator of the system 400 using a user input interface (for example, a keyboard and/or a mouse coupled to the processing device). The instructions may be configured using some suitable form, for example, a programming language or script such as LabVIEW™, Andor Solis Basic™, MetaMorph™, Molecular Devices™, Universal Imaging™, or some other suitable method.

The process 600A illustrated in FIG. 11 describes recording at high speed the dynamics of cellular and/or biochemical processes of a population of cells of a biological sample. At 602, the displacement of a pulsed laser beam is manipulated. The pulsed laser beam may be generated by the laser source 410 and/or 412.

The shape of the pulsed laser beam may be modified at 604. There may be some lens to obtain an arbitrary shape.

At 606, the spectrum of the pulsed laser beam is dispersed. For example, the dispersive element 406 may spatially disperse the spectrum of the pulsed laser beam that is applied to the biological sample.

A multiphoton excitation area is generated using the pulsed laser beam at 608. For example, the first element 408 refocuses the spectrum of the pulsed laser beam dispersed by the dispersive element 406 into the focal region of the first element 408, generating the multiphoton excitation area.

The multiphoton excitation area is applied to a biological sample at 610. For example, the first element 408 images the multiphoton excitation area in a biological sample that is placed in the target device 432. The multiphoton excitation area imaged in the biological sample may correspond to, for example, one of the multiphoton excitation patterns 502b, 504b or 506b, depending on the configuration of the first element 404.

At 612, information about the cellular or biochemical dynamics of the biological sample is captured at single-cell resolution in synchrony with the shape and spatial displacement of the pulsed laser beam. For example, one or more of the components 422, 424, 426 or 428 may be used to record information about cellular or other biochemical activity of a population of cells of the biological sample in the target device 432. The information, for example, images, may be recorded for the multiphoton excitation area that is imaged in the biological sample using one or more of the components 406, 408, 410 or 412.

The process 600B illustrated in FIG. 12 describes the generation and processing of the pulsed laser beam before manipulation by the manipulating element. In some implementations, the process 600B may be used in conjunction with the process 600A, while in other implementations they may be used separately.

At 622, the pulsed laser beam is generated using a laser source. For example, the laser source 410 may be operated to generate a laser beam with a pulse duration in the range of picoseconds or femtoseconds.

The pulsed laser beam is amplified at 624. For example, the pulsed laser amplifier 412 may include a regenerative amplifier that may be used to receive the pulsed laser beam generated by the laser source 410 and increase the power of the pulsed laser beam.

In some implementations, the pulsed laser beam may be tuned to an excitation wavelength of a molecular reporter associated with the biological sample at 626. For example, the system 400 may include optical elements 416a and/or 416b that may be used to tune the pulsed laser beam to an excitation wavelength of the molecular reporter (for example, but not limited to, NLS-GCaMP5K) that is used to note the activity associated with the cells or biochemical processes of the biological sample.

In some implementations, the power of the pulsed laser beam is attenuated at 628. For example, a motorized half-wave plate and a polarizing beam splitter with a shutter may be coupled to the pulsed laser source 410 and/or 412, and used to attenuate the power of the pulsed laser beam to a range in the order of units of micro-Joules.

In some implementations, the cross-sectional area of the pulsed laser beam is expanded at 630. For example, one or more optical elements, such as 418a or 418b, may be used to adjust the cross-sectional area of the pulsed laser beam, which may be applied at the dispersive element 406. The optical elements 418a and/or 418b may expand the diameter of the pulsed laser beam from diameter in some implementations, while in other implementations, the optical element may contract the diameter of the pulsed laser beam, or adjust the shape of the pulsed laser beam in some other arbitrary form.

The pulsed laser beam is provided for manipulation, modification and/or dispersion at 632. For example, the second element 408 may image the pulsed laser beam dispersed by the dispersive element 406 in the biological sample to form the multiphoton excitation area in the biological sample. The shape and/or position of the multiphoton excitation area in the biological sample may be adjusted.

The process 600C illustrated in FIG. 13 describes the detection and recording of information about the dynamics of cellular or biochemical processes of the biological sample based on the multiphoton excitation area formed in the biological sample. In some implementations, the process 600C may be used in conjunction with the process 600A or the process 600B, or both, while in other implementations the different processes may be used separately.

At 642, the signal associated with cellular dynamics of the biological sample is separated from the excitation light. For example, the second element 422 may separate a fluorescence signal corresponding to the molecular reporter used with the biological sample from the multiphoton excitation area light generated by the pulsed laser beam.

The separated signal is propagated on to a detection plane at 644. For example, the third element 424 may propagate the signal separated by the second element 422 onto an imaging sensor of the detector 426.

At 646, information about the cellular or biochemical process dynamics of the biological sample is captured at single-cell resolution. For example, the detector 426 may generate images of the dynamics of cellular or biochemical processes of the biological sample using an image sensor. The images may be generated with a resolution in the order of a single cell. These images may be captured using scripts and processed, or stored for post-processing.

The disclosed and other examples may be implemented as one or more computer program products, i.e., one or more modules of computer program instructions encoded on a computer readable medium for execution by, or to control the operation of, data processing apparatus. The implementations can include single or distributed processing of algorithms. The computer readable medium can be a machine-readable storage device, a machine-readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code executed by the that creates an execution environment for the computer program in question, for example, but not limited to, code that constitutes processor firmware, a protocol stack, a database management system, an operating system, or a combination of one or more of them.

A system may encompass all apparatus, devices, and machines for processing data, including by way of example a programmable processor, a computer, or multiple processors or computers. A system can include, in addition to hardware, code executed by the hardware that creates an execution environment for the computer program in question, for example, but not limited to, code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (for example, but not limited to, one or more scripts stored in a markup language document), in a single file dedicated to the program in question, or in multiple coordinated files (for example, but not limited to, files that store one or more modules, sub programs, or portions of code). A computer program can be deployed for execution on one computer or on multiple computers that are located at one site or distributed across multiple sites and interconnected by a communications network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, for example, but not limited to, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory, or a random access memory, or both. The essential elements of a computer can include a processor for performing instructions and one or more memory devices for storing instructions and data. Generally, a computer can also include, or be operatively coupled to receive data from or transfer data to, or both, one or more mass storage devices for storing data, for example, magnetic, magneto optical disks, or optical disks. However, a computer need not have such devices. Computer readable media suitable for storing computer program instructions and data can include all forms of nonvolatile memory, media and memory devices, including by way of example semiconductor memory devices, for example, but not limited to, EPROM, EEPROM, and flash memory devices; magnetic disks, such as internal hard disks or removable disks; magneto optical disks; and CD ROM and DVD-ROM disks. The processor and the memory can be supplemented by, or incorporated in, special purpose logic circuitry.

While this document may describe many specifics, these should not be construed as limitations on the scope of an invention that is claimed or of what may be claimed, but rather as descriptions of features specific to particular embodiments. Certain features that are described in this document in the context of separate implementations can also be implemented in combination in a single embodiment. Conversely, various features that are described in the context of a single implementations can also be implemented in multiple implementations separately or in any suitable sub-combination. Moreover, although features may be described above as acting in certain combinations and even initially claimed as such, one or more features from a claimed combination in some cases can be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications, and enhancements to the described examples and implementations and other implementations can be made based on what is disclosed.

We claim:

1. A device for recording the dynamics of cellular processes, the device comprising:
    one or more dispersive elements configured to receive a pulsed laser beam with a spectrum of different wavelengths and disperse the spectrum of the pulsed laser beam;
    one or more first elements configured to:
        receive the dispersed spectrum of the pulsed laser beam, and
        generate a multiphoton excitation area in a biological sample by re-overlapping in time and space the dispersed spectrum of the pulsed laser beam on an area in the biological sample; and
    a molecular reporter configured to artificially introduce labeling molecules into the biological sample,
    wherein the device is configured to record at high speed changes of cellular and biochemical processes of a population of cells of the biological sample based on generation of the multiphoton excitation area in the biological sample and subsequent optical readout of light emission properties of the artificially-introduced labeling molecules.

2. The device of claim 1, wherein the high speed recording includes near-simultaneous imaging of the cellular or biochemical changes within a single plane of the biological sample.

3. The device of claim 2, wherein the near-simultaneous imaging includes imaging in an order of seconds to picoseconds.

4. The device of claim 1, wherein the multiphoton excitation area includes a wide-field excitation disc with one of a predetermined diameter or a predetermined axial confinement, wherein the predetermined diameter or the predetermined axial confinement is user-configurable, and wherein at least one of the predetermined diameter or the predetermined axial confinement is in a range that is in an order of 1 μm to 1 mm.

5. The device of claim 1, wherein a first element includes at least one of a grating, a prism, a lens or a microscope objective lens that are configured to generate the multiphoton excitation area in the biological sample by imaging onto the biological sample an area on the dispersive element illuminated by the pulsed laser beam.

6. The device of claim 1, wherein the multiphoton excitation area comprises a disc shaped excitation area of the dispersed spectrum of the pulsed laser beam, and wherein spectral components of the pulsed laser beam overlap in time and space in a focal region of the first element.

7. The device of claim 1, further comprising:
    a first amplifier that is configured to amplify the pulsed laser beam, wherein the pulsed laser beam amplified by the first amplifier is used at the dispersive element;
    a wavelength tuning element that is configured to tune the central wavelength of the pulsed laser beam amplified by the first amplifier to an excitation wavelength of the labeling molecules artificially-introduced by the molecular reporter into the biological sample; and a motorized half-wave plate and a polarizing beam splitter with a shutter that are configured to attenuate the power of the pulsed laser beam at an output of the wavelength tuning element, wherein the molecular reporter is configured to facilitate recording of the cellular or biochemical changes of the biological sample.

8. The device of claim 7, wherein the first amplifier includes a regenerative amplifier.

9. A method for high-speed imaging of cellular or biochemical changes of a population of cells of a biological sample, comprising:
providing a pulsed laser beam with a spectrum of different wavelengths at a dispersive element;
dispersing the spectrum of the pulsed laser beam using the dispersive element;
generating, using a first element, a multiphoton excitation area based on the dispersed spectrum of the pulsed laser beam;
applying, by the first element, the multiphoton excitation area to a biological sample;
artificially introducing labeling molecules into the biological sample; and
capturing, using an imaging detector array, information about the cellular or biochemical changes of a population of cells of the biological sample included in the multiphoton excitation area by optically reading light emission properties of the artificially-introduced labeling molecules, wherein the information about the cellular or biochemical changes are captured in parallel at a resolution of a single cell.

10. The method of claim 9, wherein providing the pulsed laser beam at the dispersive element comprises:
generating the pulsed laser beam using a laser source;
amplifying, using a first amplifier, the pulsed laser beam;
tuning, using a wavelength tuning element, central wavelength of the pulsed laser beam amplified by the first amplifier to an excitation wavelength of the labeling molecules artificially-introduced by a molecular reporter that produces a signal associated with the cellular or biochemical changes of the cells of the biological sample; and
providing the pulsed laser beam tuned by the wavelength tuning element at the dispersive element.

11. The method of claim 10, wherein providing the pulsed laser beam tuned by the wavelength tuning element at the dispersive element further comprises:
attenuating the power of the pulsed laser beam tuned by the wavelength tuning element using an attenuating element;
modulating a cross-sectional area of the pulsed laser beam using a second optical element; and
providing the pulsed laser beam with the modulated cross-sectional area at the dispersive element.

12. The method of claim 11, wherein the attenuating element includes one of a half-wave plate and a beam splitter, or a shutter.

13. The method of claim 9, wherein the first element includes at least one of a relay lens or a microscope objective that are configured to generate the multiphoton excitation area in a focal region of the microscope objective.

14. The method of claim 9, wherein the labeling molecules are configured to readout at least one of calcium concentrations in the cells, or changes to calcium concentrations in the cells.

15. The method of claim 14, wherein the labeling molecules comprise a nuclear-localized, genetically encoded calcium indicator which enables recording the dynamics of individual cells of the biological sample.

16. The method of claim 9, wherein the labeling molecules comprise proteins that are expressed by the cells by introducing genetic information to the cells.

17. The method of claim 9, wherein the labeling molecules are configured to report on at least one of membrane voltage of the cells, or changes to the membrane voltage of the cells.

18. The method of claim 9, wherein the labeling molecules are configured to report on synaptic activity in the cells.

19. The method of claim 9, wherein the labeling molecules are configured to report on metabolic activity in the cells.

20. The method of claim 9, wherein the labeling molecules are configured to report on enzymatic activity in the cells.

21. The method of claim 9, wherein the labeling molecules are configured to bind to at least one of naturally available proteins in the cells, or other molecules in the cells.

22. The method of claim 9, wherein the labeling molecules are configured to report on a stage of the cell cycle.

23. A device for recording the dynamics of cellular processes, the device comprising:
one or more manipulating elements configured to manipulate spatial or angular displacement of a pulsed laser beam that includes a spectrum of different wavelengths;
one or more first elements configured to modify the shape of the pulsed laser beam;
one or more dispersive elements configured to disperse the spectrum of the pulsed laser beam;
one or more second elements configured to generate a multiphoton excitation area based on the dispersed spectrum of the pulsed laser beam and apply the multiphoton excitation area to a biological sample; and
a molecular reporter configured to artificially introduce labeling molecules into the biological sample,
wherein the device is configured to record at high-speed changes of cellular or biochemical processes of a population of cells of the biological sample based on application of the multiphoton excitation area to the biological sample and subsequent optical readout of light emission properties of the artificially-introduced labeling molecules.

24. The device of claim 23, wherein a first element includes a spherical lens that is configured to shape an area on the dispersive element used by the manipulating device to generate a trajectory on the dispersive element that corresponds to the multiphoton excitation area in the biological sample.

25. The device of claim 23, wherein the multiphoton excitation area is disc shaped with a predetermined axial confinement that is user-configurable in a range in an order of 1 μm to 1 mm.

26. The device of claim 25, wherein the one or more second elements is configured to vary the diameter of the disc shaped excitation area.

27. The device of claim 23, wherein the device is configured to perform the high-speed recording at single-cell spatial resolution for a predetermined time period.

28. A device comprising:
one or more manipulating elements configured to manipulate spatial or angular displacement of a pulsed laser beam that includes a spectrum of different wavelengths;
one or more first elements configured to modify the shape of the pulsed laser beam;

one or more dispersive elements configured to disperse the spectrum of the pulsed laser beam; and one or more second elements configured to generate a multiphoton excitation area based on the dispersed spectrum of the pulsed laser beam and apply the multiphoton excitation area to a biological sample, wherein the device is configured to record at high-speed changes of cellular or biochemical processes of a population of cells of the biological sample based on application of the multiphoton excitation area to the biological sample, and wherein the device further comprises a detection section for detecting the changes of the cellular or biochemical processes of the cells of the biological sample, the detection section comprising:

a third element that is configured to separate a signal associated with the changes of the cellular or biochemical processes from the pulsed laser beam; and a fourth element that is configured to propagate the separated signal onto a detection plane of a detector.

29. The device of claim 28, wherein the detection section detector is an imaging detector array that is configured to generate images of the cellular or biochemical changes of the population of cells of the biological sample.

\* \* \* \* \*